(12) United States Patent
Barbut

(10) Patent No.: US 6,878,140 B2
(45) Date of Patent: *Apr. 12, 2005

(54) METHODS FOR FLOW AUGMENTATION IN PATIENTS WITH OCCLUSIVE CEREBROVASCULAR DISEASE

(75) Inventor: Denise Barbut, New York, NY (US)

(73) Assignee: CoAxia, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/431,051

(22) Filed: May 6, 2003

(65) Prior Publication Data

US 2003/0199802 A1 Oct. 23, 2003

Related U.S. Application Data

(62) Division of application No. 09/559,307, filed on Apr. 25, 2000, now Pat. No. 6,558,356, which is a division of application No. 09/232,438, filed on Jan. 15, 1999, now Pat. No. 6,161,547.

(51) Int. Cl.[7] .................. A61M 31/00; A61M 37/00; A61B 19/00; A61B 17/00
(52) U.S. Cl. .............. 604/509; 604/500; 604/4.01; 604/6.14; 606/190; 128/898
(58) Field of Search ................ 604/500–509, 604/4.01–6.14, 102.03, 4, 5, 89, 96.01, 102.02, 118, 171, 264, 523, 27, 35, 912, 915, 173, 6.16, 284, 104, 102.01; 128/898; 606/194–200, 190; 607/105; 422/44–45; 623/1.2

(56) References Cited

U.S. PATENT DOCUMENTS

| | | | |
|---|---|---|---|
| 4,248,224 A | | 2/1981 | Jones |
| 4,610,656 A | | 9/1986 | Mortensen |
| 4,619,639 A | | 10/1986 | Nosé et al. |
| 4,712,551 A | | 12/1987 | Rayhanabad |
| 4,731,055 A | | 3/1988 | Melinyshyn et al. |
| 4,804,359 A | | 2/1989 | Grunwald et al. |
| RE34,077 E | | 9/1992 | Segall et al. |
| 5,226,430 A | * | 7/1993 | Spears et al. ............... 128/898 |
| 5,348,015 A | | 9/1994 | Moehring et al. |
| 5,374,239 A | | 12/1994 | Mischenko |
| 5,458,574 A | | 10/1995 | Machold et al. |
| 5,695,519 A | | 12/1997 | Summers et al. |
| 5,827,222 A | | 10/1998 | Klatz et al. |
| 5,876,367 A | | 3/1999 | Kaganov et al. |
| 6,042,559 A | | 3/2000 | Dobak, III |
| 6,048,331 A | | 4/2000 | Tsugita et al. |
| 6,146,370 A | * | 11/2000 | Barbut ....................... 604/500 |
| 6,161,547 A | * | 12/2000 | Barbut ....................... 128/898 |
| 6,165,199 A | * | 12/2000 | Barbut ....................... 606/200 |
| 6,312,444 B1 | * | 11/2001 | Barbut ....................... 606/200 |
| 6,413,235 B1 | * | 7/2002 | Parodi ........................ 604/104 |

(Continued)

OTHER PUBLICATIONS

R.S. Veeragandham et al., "Experience With Antegrade Bihemispheric Cerebral Perfusion in Aortic Arch Operations", Mar. 1998, Ann. Thorac. Surg., 1998, 66:493–9.

(Continued)

Primary Examiner—Nicholas D. Lucchesi
Assistant Examiner—Roz Maiorino
(74) Attorney, Agent, or Firm—O'Melveny & Myers LLP

(57) ABSTRACT

The invention provides a method for augmenting circulation in a patient having carotid stenosis. An elongate tubular member is provided having a lumen communicating with a port at a distal end. The tubular member is inserted into a peripheral artery and the distal port is advanced into a first carotid artery substantially free of a lesion where the patient possesses a second carotid artery substantially occluded by a lesion. Blood is perfused into the first carotid artery through the tubular member. Contralateral flow is augmented to improve perfusion to an ischemic region distal to the carotid stenosis. Angioplasty and stenting can be used to open the lesion in the second carotid artery.

18 Claims, 15 Drawing Sheets

U.S. PATENT DOCUMENTS

| | | | |
|---|---|---|---|
| 6,605,074 B2 * | 8/2003 | Zadno-Azizi et al. | 604/509 |
| 6,699,231 B1 * | 3/2004 | Sterman et al. | 604/509 |
| 6,736,790 B2 * | 5/2004 | Barbut et al. | 604/6.13 |
| 2001/0049517 A1 * | 12/2001 | Zadno-Azizi et al. | 604/509 |
| 2002/0052620 A1 * | 5/2002 | Barbut | 606/190 |
| 2002/0091407 A1 * | 7/2002 | Zadno-Azizi et al. | 606/200 |
| 2002/0173815 A1 * | 11/2002 | Hogendijk et al. | 606/194 |

OTHER PUBLICATIONS

L. Testolin et al., "Moderately hypothermic cardiopulmonary bypass and selective cerebral perfusion in ascending aorta and aortic arch surgery. Preliminary experience in twenty–two patients", Aug. 1998, Cardiovascular Surgery, vol. 6, No. 4., pp. 398–405, Great Britain.

Hikaru Matsuda, Md, et al., "Surgery for Aortic Arch Aneurysm With Selective Cerebral Perfusion and Hypothermic Cardiopulmonary Bypass", Sep. 1989, Circulation, Supp. I, vol. 80, No. 3, pp. I-243-248.

Schwartz, Arthur E., M.D. et al., "Isolated Cerebral Hypothermia by Single Carotid Artery Perfusion of Extracorporeally Cooled Blood in Baboons", Sep. 1996, Neurosurgery, vol. 39, No. 3, pp. 577–582.

Schwartz, Arthur E., M.D., et al., "Selective Cerebral Hypothermia by Means of Transfemoral Internal Carotid Artery Catheterization", Nov. 1996, Radiology, vol. 201, No. 2, pp. 571–572.

C. Maas, et al., "Intermittent antegrade/selective cerebral perfusion during circulatory arrest for repair of the aortic arch", 1997, Perfusion, 12:127–132.

Bachet, Jean, Md, et al., "Cold cerebroplegia", Jul. 1991, J. Thorac. Cardiovasc. Surg., 1991;102:85–94.

* cited by examiner

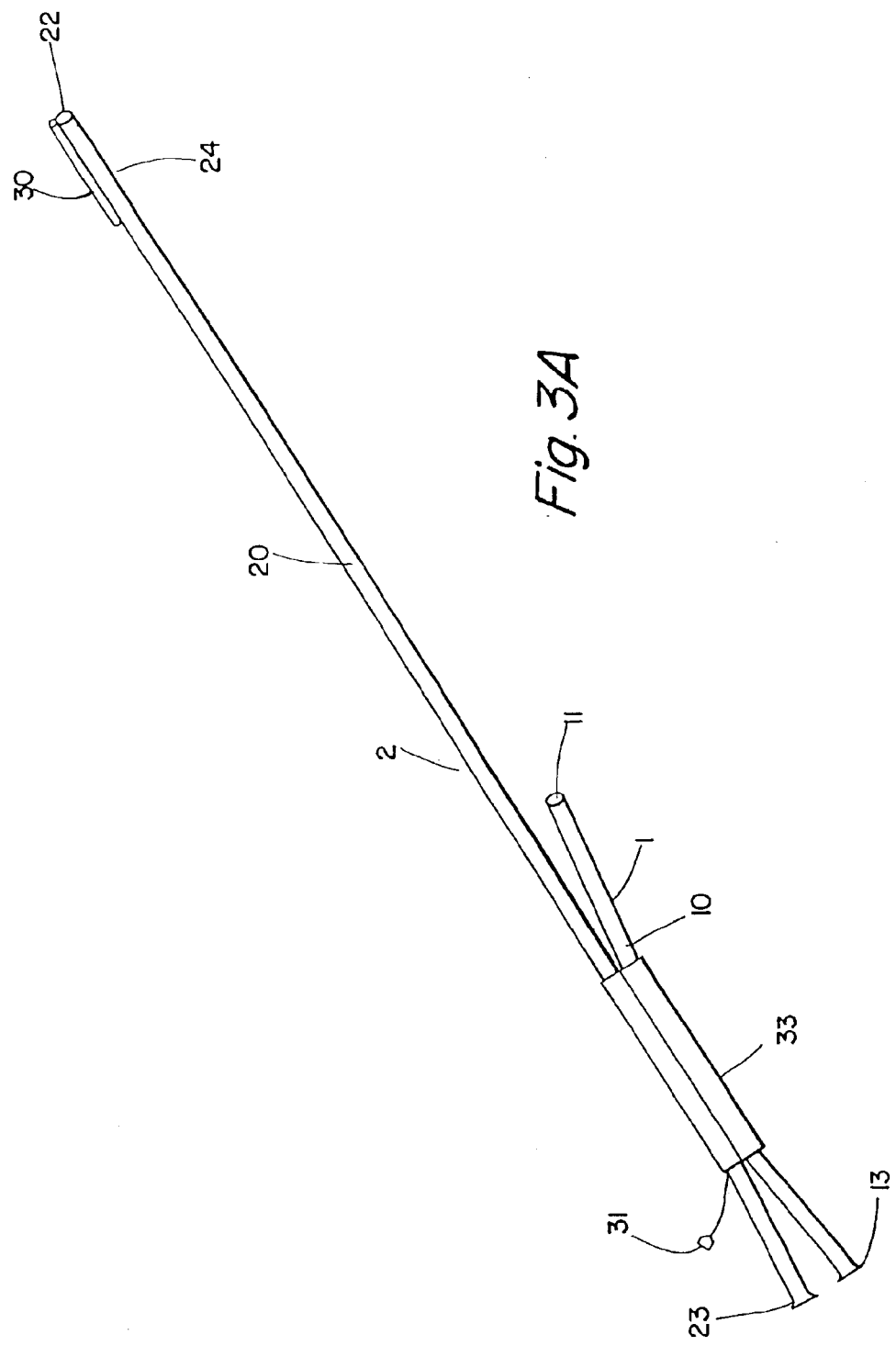

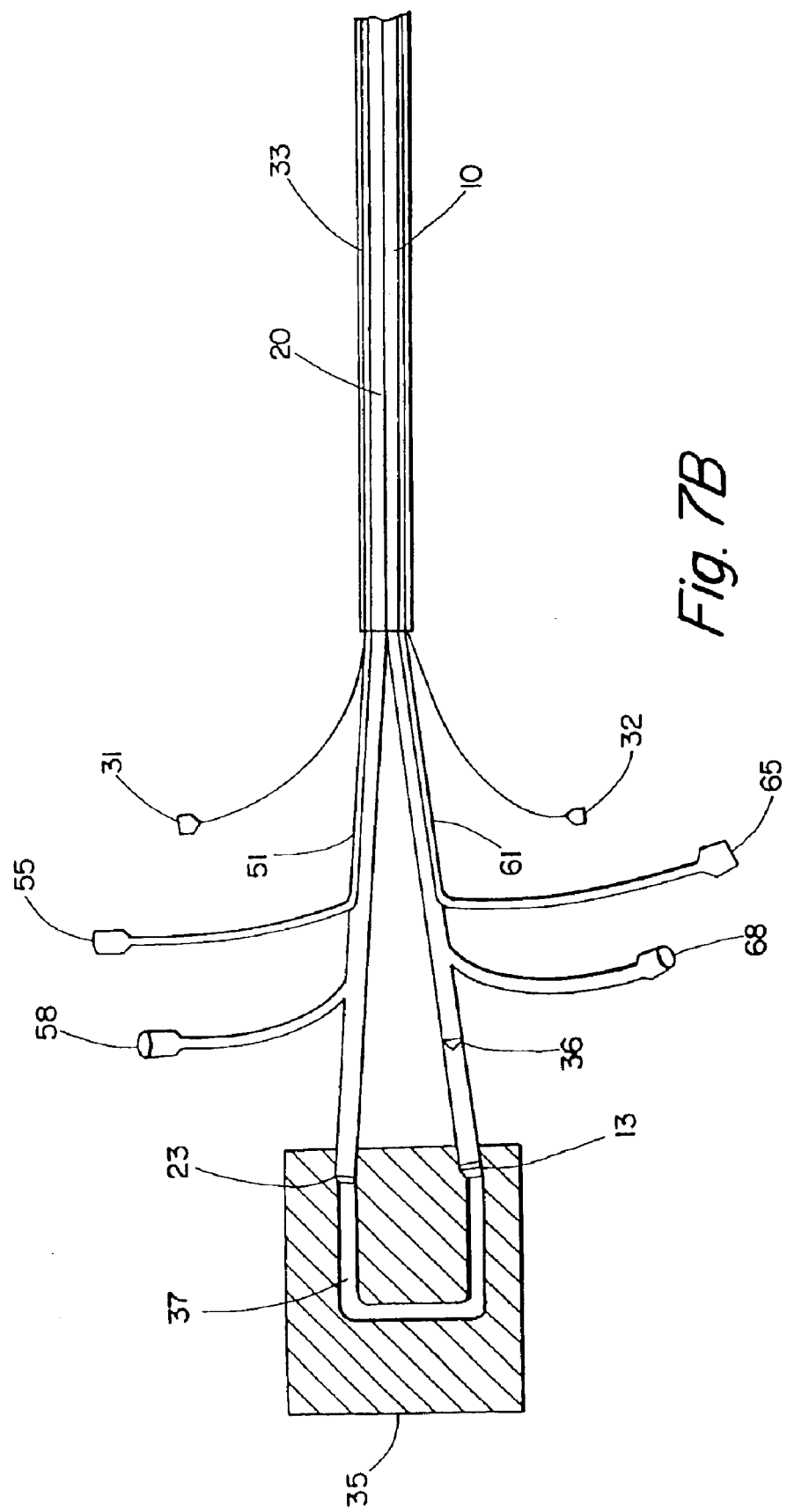

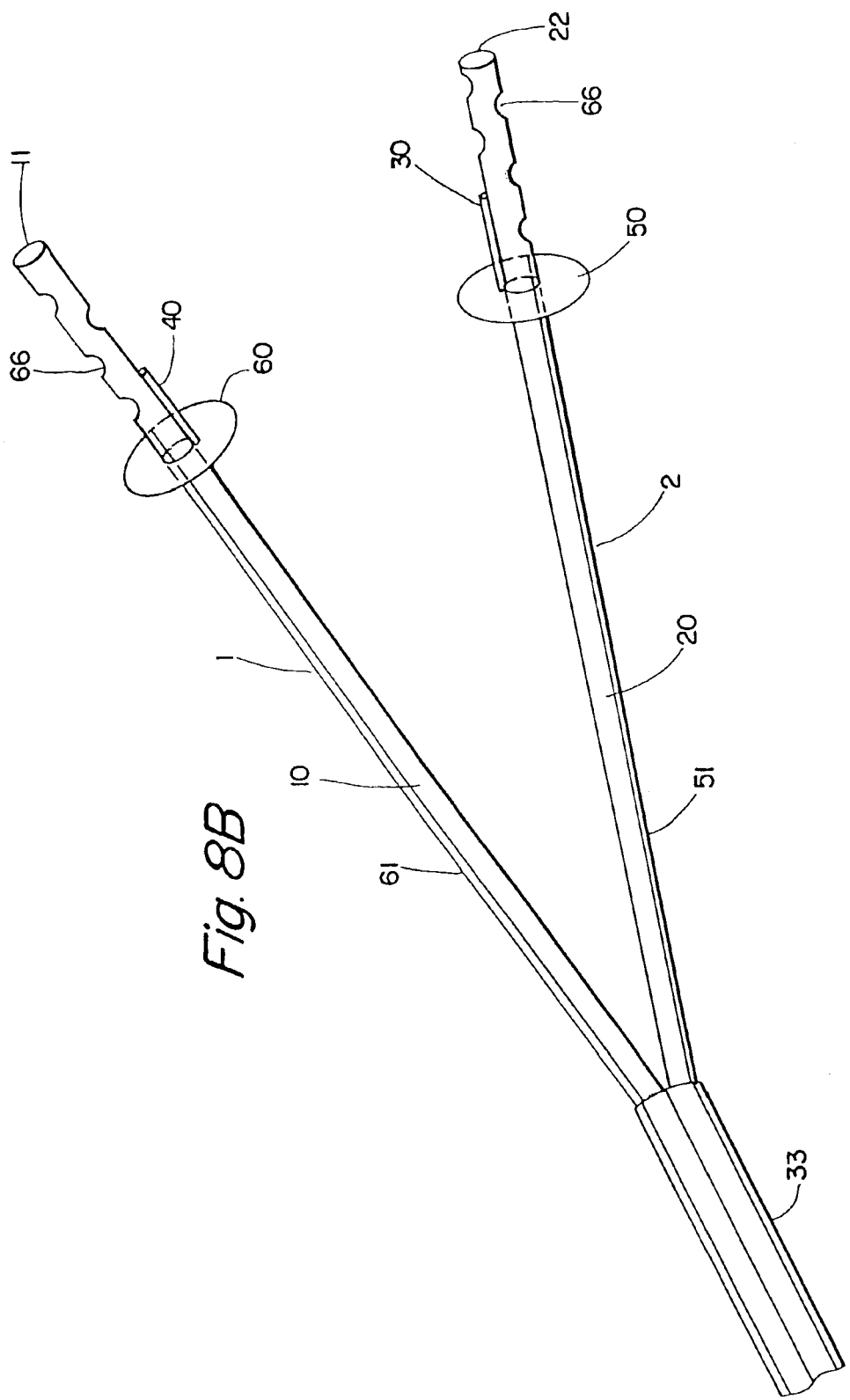

METHODS FOR FLOW AUGMENTATION IN PATIENTS WITH OCCLUSIVE CEREBROVASCULAR DISEASE

This is a divisional application of application Ser. No. 09/559,307, filed Apr. 25, 2000, now U.S. Pat. No. 6,558,356, which is a divisional application of application Ser. No. 09/232,438, filed Jan. 15, 1999, now U.S. Pat. No. 6,161,547, all of which are incorporated herein by reference in their entirety.

FIELD OF THE INVENTION

The present invention generally relates to medical devices useful in treating patients with acute stroke or occlusive cerebrovascular disease. More specifically, the invention provides an extra/intracranial device capable of removing blood from a peripheral artery or symptomatic carotid artery and returning the blood to the contralateral carotid artery, thereby providing a means of augmenting the collateral vasculature and maintaining perfusion distal to the offending lesion. The device may employ neuroprotective agents, hypothermic perfusion, and an atherectomy device or an extracorporeal pumping mechanism to remove a vascular occlusion and reestablish cerebral perfusion.

BACKGROUND OF THE INVENTION

Stroke is the third most common cause of death in the United States and the most disabling neurologic disorder. Approximately 700,000 patients suffer from stroke annually. Stroke is a syndrome characterized by the acute onset of a neurological deficit that persists for at least 24 hours, reflecting focal involvement of the central nervous system, and is the result of a disturbance of the cerebral circulation. Outcome following stroke is influenced by a number of factors, the most important being the nature and severity of the resulting neurologic deficit. The patient's age, the cause of stroke, and coexisting medical illness also affect prognosis. Overall, less than 80% of patients with stroke survive for at least 1 month, and approximately 35% have been cited for the 10-year survival rates. Of patients who survive the acute period, up to 75% regain independent function, while approximately 15% require institutional care.

Hemorrhagic stroke accounts for 20% of the annual stroke population. Hemorrhagic stroke often occurs due to rupture of an aneurysm or arteriovenous malformation bleeding into the brain tissue, resulting in cerebral infarction. The remaining 80% of the stroke population are hemispheric ischemic strokes and are caused by occluded vessels that deprive the brain of oxygen-carrying blood. Ischemic strokes are often caused by emboli or pieces of thrombotic tissue that have dislodged from other body sites or from the cerebral vessels themselves to occlude in the narrow cerebral arteries more distally. When a patient presents with neurological symptoms and signs which resolve completely within 1 hour, the term transient ischemic attack (TIA) is used. Etiologically, TIA and stroke share the same pathophysiologic mechanisms and thus represent a continuum based on persistence of symptoms and extent of ischemic insult.

When a patient presents with neurological deficit, a diagnostic hypothesis for the cause of stroke can be generated based on the patient's history, a review of stroke risk factors, and a neurologic examination. If an ischemic event is suspected, a clinician can tentatively assess whether the patient has a cardiogenic source of emboli, large artery extracranial or intracranial disease, small artery intraparenchymal disease, or a hematologic or other systemic disorder. A head CT scan is often performed to determine whether the patient has suffered an ischemic or hemorrhagic insult. Blood would be present on the CT scan in subarachnoid hemorrhage, intraparenchymal hematoma, or intraventricular hemorrhage.

Traditionally, emergent management of acute ischemic stroke consists of mainly general supportive care, e.g. hydration, monitoring neurological status, blood pressure control, and/or anti-platelet or anti-coagulation therapy. In June 1996, the Food and Drug Administration approved the use of Genentech Inc.'s thrombolytic drug, tissue plasminogen activator (t-PA) or Activase®, for treating acute stroke. In a randomized, double-blind trial, the National Institute of Neurological Disorders and t-PA Stroke Study, there was a statistically significant improvement in stoke scale scores at 24 hours in the group of patients receiving intravenous t-PA within 3 hours of the onset of an ischemic stroke. Since the approval of t-PA, an emergency room physician could, for the first time, offer a stroke patient an effective treatment besides supportive care.

However, treatment with systemic t-PA is associated with increased risk of intracerebral hemorrhage and other hemorrhagic complications. Patients treated with t-PA were more likely to sustain a symptomatic intracerebral hemorrhage during the first 36 hours of treatment. The frequency of symptomatic hemorrhage increases when t-PA is administered beyond 3 hours from the onset of a stroke. Besides the time constraint in using t-PA in acute ischemic stroke, other contraindications include the following: if the patient has had a previous stroke or serious head trauma in the preceding 3 months, if the patient has a systolic blood pressure above 185 mm Hg or diastolic blood pressure above 110 mmHg, if the patient requires aggressive treatment to reduce the blood pressure to the specified limits, if the patient is taking anticoagulants or has a propensity to hemorrhage, and/or if the patient has had a recent invasive surgical procedure. Therefore, only a small percentage of selected stroke patients are qualified to receive t-PA.

New devices and methods are thus needed in treating patients with acute ischemic stroke and occlusive cerebrovascular disease, in treating symptomatic patients with embolization or hemodynamic compromise, or in stroke prevention, e.g., patients with incidental finding of asymptomatic carotid lesion undergoing cardiothoracic surgery, which improve a patient's neurological function and quality of life without causing significant side effect, and can be used in patients with contraindication to using t-PA.

SUMMARY OF THE INVENTION

The invention provides devices and methods for treatment of acute ischemic stroke and occlusive cerebrovascular disease by taking advantage of the collateral cerebral circulation. Anastomoses between the cerebral arteries provide alternative pathways in which blood can reach a given region of the brain besides the predominant supplying artery. At the base of the brain close to the sella turcica, circulus arteriosus cerebri, or Circle of Willis, connects the vertebral and internal carotid arteries to each other and to the vessels of the opposite side. When occlusion of a blood vessel interrupting the flow of blood to a specific region of the brain occurs, survival of the brain tissue and therefore severity of a patient's neurological deficit depend on the number and size of its collateral arteries. Effective stroke therapies therefore rely on the physicians' ability to respond to treatment quickly, since the longer the brain is deprived of blood flow, the greater the damage that occurs. The devices and methods of the present invention are used to augment contralateral blood flow across the Circle of Willis to improve and maintain perfusion to an ischemic region distal to an occluded intra/extracranial cerebral artery, and thus can be utilized in stroke patients immediately after onset of symptoms to maintain viability of the cerebral tissue until the obstructing lesion is removed by an intervention or resolved with time (more than one half of the occluding thrombi usually lyse themselves in a few days).

One embodiment of the medical device comprises first and second elongate tubes. Each tube has a manometer at a distal end and a lumen communicating with a port at the distal end. An expandable occlusive member is optionally mounted on either or both tubular members proximal to the distal port and is adapted to expand to engage the lumen of an intracranial or extracranial artery. A proximal end of each tubular member attaches to an oxygenator or a pump for aspirating blood through the first tube and perfusing the blood through the second tube.

In another embodiment, each tube has an additional lumen which communicates with a port distal to the balloon occluder for infusing fluid and pharmaceutical agents, such as a neuroprotective agent or heparin.

In still another embodiment, the first and second tubes are carried within the lumen of an elongate catheter. The lumen of either tubular member communicates with one or a plurality of perfusion ports and is adapted for aspiration or infusion of blood.

In still another embodiment, the proximal end of either tubular member includes a blood filter which entraps any thromboembolic debris flowing through the circuit before blood is perfused to an artery.

In still another embodiment, the first tubular member, which is adapted for insertion into an occluded carotid or cerebral artery, comprises an additional lumen adapted for introduction of an atherectomy device for removing occlusive lesions in the artery.

The invention also provides methods for augmenting contralateral circulation in a patient with occlusive cerebrovascular disease using the devices described above. The methods can be used to perfuse and maintain blood flow to an ischemic region distal to an occluding lesion in patients who are symptomatic due to embolization of a cerebral artery lesion or hemodynamic compromise caused by the lesion. The methods can also be used in stroke prevention, e.g., in asymptomatic patients who are undergoing a major surgery such as cardiothoracic surgery and are found incidentally to have significant flow limiting cerebral lesions during cardiac catheterization or angiogram.

In a first method, the distal end of the first tubular member is inserted through an incision into a peripheral artery, such as a femoral artery. The occluding lesion in the symptomatic artery is localized with an angiogram or intravascular ultrasound (IVUS). With assistance of a guide wire, the distal end of the second tubular member is inserted through the same incision or a different incision into the contralateral carotid artery. Oxygenated blood is aspirated from the artery through the lumen and port of the first tubular member and perfused into the contralateral carotid artery through the lumen and port of the second tubular member. An expandable occluder, e.g., a balloon occluder, may be expanded on the second tubular member proximal to the distal port to control the flow rate more effectively. In this manner, augmented contralateral perfusion provides enhanced reversal of blood flow across the Circle of Willis to compensate for the sudden decrease of flow in the occluded artery.

In another method, the distal end of the first tubular member is inserted through an incision on a peripheral artery, such as a femoral artery, and advanced into the symptomatic carotid or cerebral artery proximal to the occluding lesion. In an emergency, the device can also be inserted into a patient's carotid artery as a direct stick after localizing the occlusion with the assistance of IVUS or standard carotid doppler and/or transcranial doppler (TCD). The distal end of the tubular member can be advanced as far as the occluding site which could be in the common carotid artery, internal carotid artery, middle cerebral artery, anterior cerebral artery, carotid siphon, terminal internal carotid artery, or any other part of the cerebral vasculature. The distal end of the second tubular member is then inserted through the same incision or a different incision, and advanced into the contralateral carotid artery. When present, the balloon occluder mounted on the first tubular member proximal to the distal port is inflated to partially occlude the arterial lumen. The proximal end of the first tubular member is attached to a vacuum pump and blood is aspirated from the symptomatic carotid artery through the lumen and port of the first tubular member, and delivered to the contralateral carotid artery through the lumen and port of the second tubular member. The flow rate can be controlled by deflating or inflating the balloon, e.g., the flow rate increases as the balloon is deflated. The augmented contralateral hemispheric blood flow, which helps to reverse flow across the Circle of Willis, provides (1) retrograde arterial collateral enhancement to the ischemic area distal to the occlusion and (2) enhances the pressure differential across the occluding lesion, which may be sufficient to dislodge any thromboembolic material. Blood aspirated from the symptomatic artery is, in certain embodiments, passed through a blood filter optionally included in the proximal end of the first or second tubular member or in the pump to entrap any embolic debris before the blood is returned to the contralateral carotid artery.

It will be understood that there are several advantages in using the devices and methods disclosed herein for management of acute stroke. For example, the devices can be used (1) in a majority of stroke patients, including those with contraindication to using systemic t-PA, (2) to administer neuroprotective agents locally into an occluded vessel, thereby providing greater local benefit and fewer systemic side effects, (3) to infuse hypothermic fluid or blood to the ischemic area, thereby providing protective focal hypothermia, (4) with standard atherectomy to remove arterial atheroma, (5) as an angioplasty device by inflating the balloon over the stenotic arterial lumen to enlarge the luminal diameter, (6) by any invasive radiologist or cardiologist, (7) in the angiogram or fluoroscopy suite available in most hospitals, (8) in treating acute stroke patients with few systemic side effects, (9) to treat symptomatic vertebral artery occlusion, (10) to maintain cerebral perfusion in patients with asymptomatic flow limiting carotid stenosis undergoing major cardiothoracic surgeries or in patients with hemodynamic instability, e.g., cardiogenic or septic shock, and (11) to maintain perfusion to the distal ischemic area, even without removal of the occlusion, to minimize neurologic damage while alternative intervention is being considered.

BRIEF DESCRIPTION OF THE DRAWINGS

FIG. 3A depicts an embodiment of the medical device for treatment of acute stroke according to the present invention.

FIG. 7B depicts a proximal region of the device shown in FIG. 7A.

FIG. 8B depicts still another embodiment of the device having balloon occluders and a plurality of perfusion ports on both tubular members.

DETAILED DESCRIPTION

The cerebral circulation is regulated in such a way that a constant total cerebral blood flow (CBF) is generally maintained under varying conditions. For example, a reduction in flow to one part of the brain, such as in acute stroke, may be compensated by an increase in flow to another part, so that CBF to any one region of the brain remains unchanged. More importantly, when one part of the brain becomes ischemic due to a vascular occlusion, the brain compensates by increasing blood flow to the ischemic area through its collateral circulation.

Figure 1:
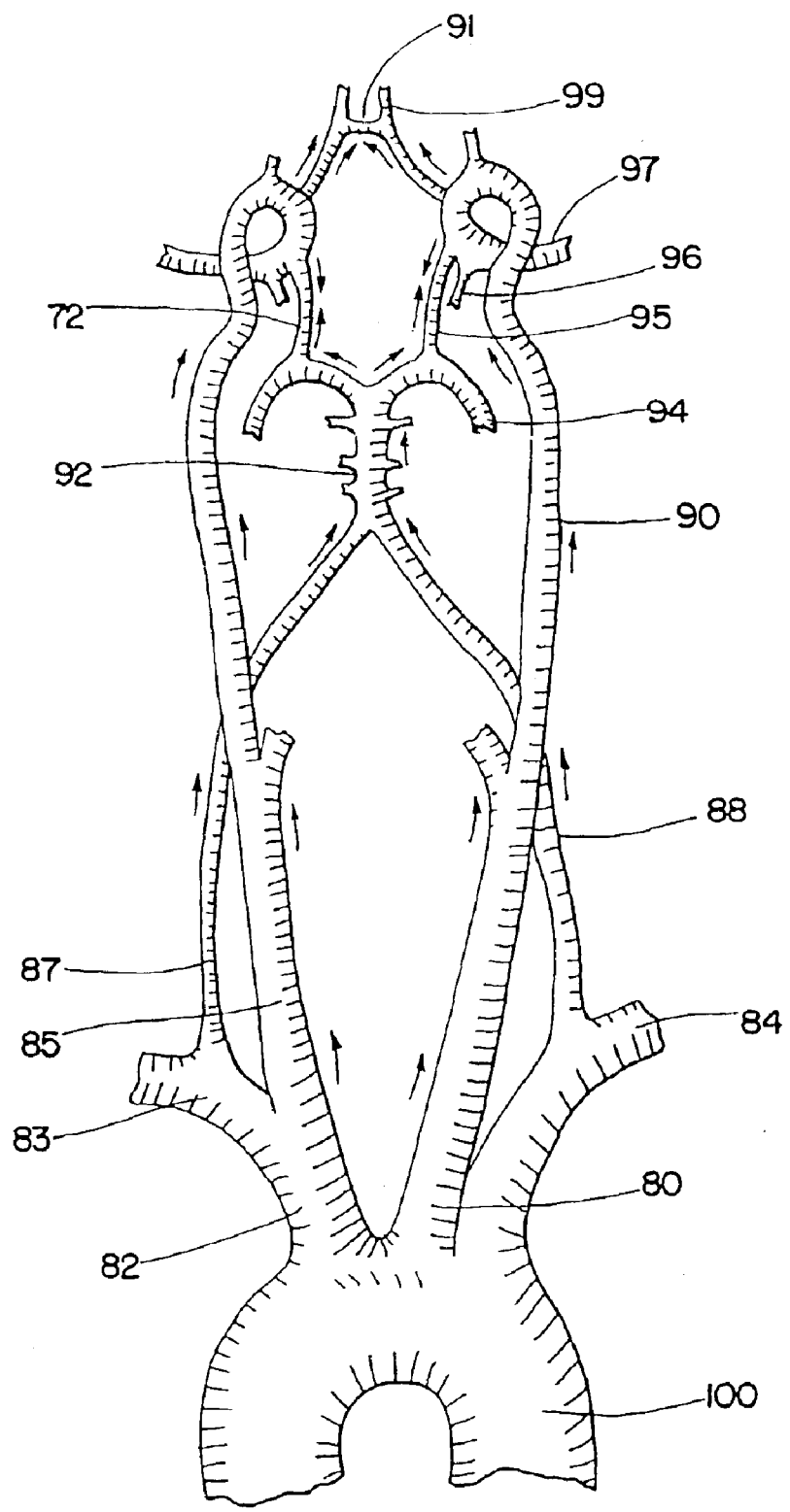
FIG. 1 depicts a normal cerebral circulation in the Circle of Willis.

FIG. 1 depicts a normal cerebral circulation and formation of Circle of Willis. Aorta 100 gives rise to right brachiocephalic trunk 82, left common carotid artery (CCA) 80, and left subclavian artery 84. The brachiocephalic artery further branches into right common carotid artery 85 and right subclavian artery 83. The left CCA gives rise to left internal carotid artery (ICA) 90 which becomes left middle cerebral artery (MCA) 97 and left anterior cerebral artery (ACA) 99. Anteriorly, the Circle of Willis is formed by the internal carotid arteries, the anterior cerebral arteries, and anterior communicating artery 91 which connects the two ACAs. The right and left ICA also send right posterior communicating artery 72 and left posterior communicating artery 95 to connect respectively with right posterior cerebral artery (PCA) 74 and left PCA 94. The two posterior communicating arteries and PCAs, and the origin of the posterior cerebral from basilar artery 92 complete the circle posteriorly.

Figure 2:
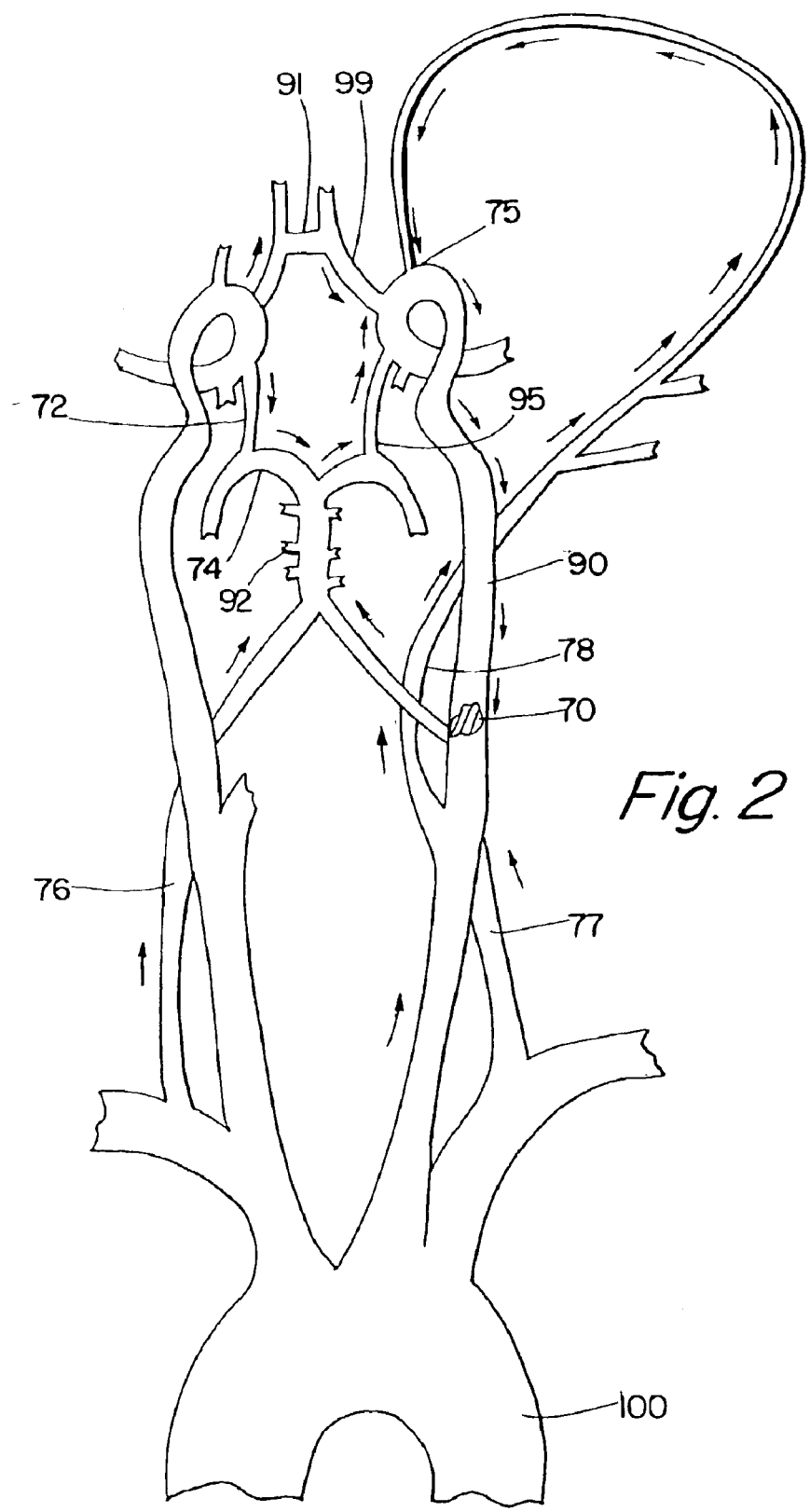
FIG. 2 depicts a reversed circulation in the Circle of Willis to compensate for an occlusion in the left internal carotid artery.

When occluding lesion 70 occurs acutely, for example, in left internal carotid artery 90, as depicted in FIG. 2, blood flow in the right cerebral arteries, left external carotid artery 78, right vertebral artery 76, and left vertebral artery 77 increases, resulting in directional change of flow through the Circle of Willis to compensate for the sudden decrease of blood flow in the left internal carotid artery. Specifically, blood flow reverses in right posterior communicating artery 72, right PCA 74, and left posterior communicating artery 95. Anterior communicating artery 91 opens, reversing flow in left ACA 99, and flow increases in the left external carotid artery, reversing flow along left ophthalmic artery 75, all of which contribute to flow in left ICA 90 distal to the occluding lesion to provide perfusion to the ischemic area distal to the occlusion.

Figure 3B:
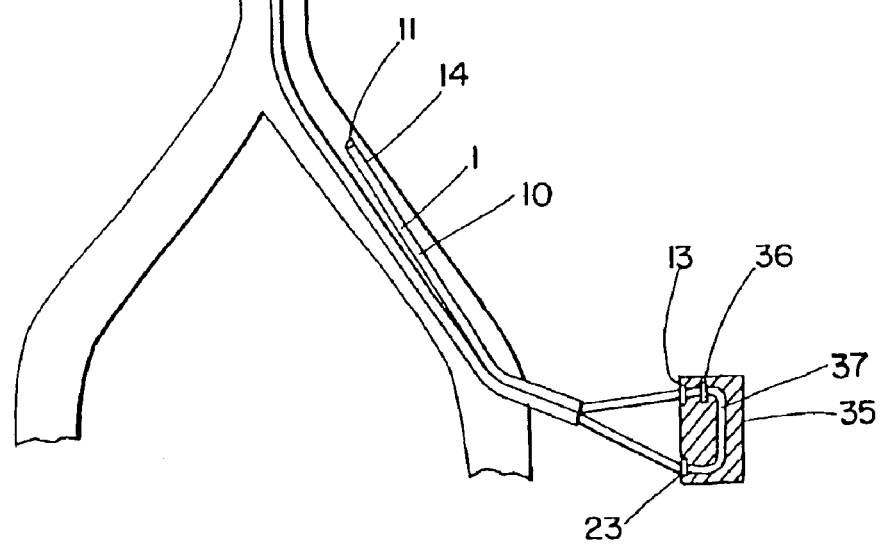
FIG. 3B depicts the device shown in FIG. 3A inserted in the contralateral carotid artery.

FIGS. 3A and 3B depict an embodiment of the device for treatment of hemispheric ischemia. The device comprises first tubular member 1 and second tubular member 2. The first tubular member has lumen 10 communicating with distal port 11 and proximal end 13 adapted for aspiration of blood. The second tubular member has lumen 20 communicating with distal port 22 and proximal end 23 adapted for perfusion of blood. The first and second tubular members are carried within a lumen of elongate catheter 33. Manometer 30, communicating proximally with sensor attachment 31, is carried at distal end 24 of the second tubular member for measuring blood pressure at the distal end. Proximal end 13 of the first tubular member and proximal end 23 of the second tubular member are adapted for attachment to a pump or oxygenator.

In using the device of FIG. 3A for treatment of hemispheric ischemia, the device is inserted through an incision on a peripheral artery, such as the left femoral artery shown in FIG. 3B. After localizing occluding lesion 70 in the left carotid artery with the assistance of IVUS or standard carotid doppler and transcranial doppler (TCD), distal end 24 of second tubular member 2 is advanced over a guide wire to position in the right carotid artery. Distal end 14 of tubular member 1 can be positioned in the descending aorta, the subclavian, the axillary, the femoral, or the iliac artery as depicted in FIG. 3B. Proximal end 13 and 23 are connected to pump 35, which aspirates blood from port 11 and lumen 10 of the first tubular member, delivering the blood through blood filter 36 included in pump conduit 37, and perfusing the blood to the right carotid artery through lumen 20 and port 22 of the second tubular member. Heparin may be administered through either proximal end of the tubular members or the pump conduit to provide anticoagulation, thereby preventing thrombi forming in the circuit. In some instances, the pump may not be necessary. Increasing blood flow in the right carotid artery results in augmented flow in the right cerebral arteries and the right vertebral artery, enhancing directional change of flow through the Circle of Willis to compensate for the sudden decrease of blood flow in the left internal carotid artery as described in FIG. 2. This method is particularly useful in situations in which increasing ipsilateral perfusion cannot be accomplished, e.g., in vessels having near total or complete occlusion. By increasing contralateral perfusion, some improvement in a patient's neurologic function may be achieved.

Figure 4:
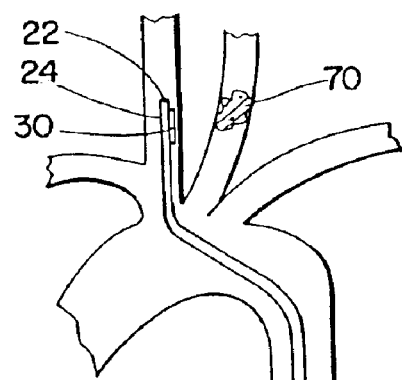
FIG. 4 depicts another embodiment of the device inserted in the carotid artery to provide contralateral flow augmentation.
Figure 4:
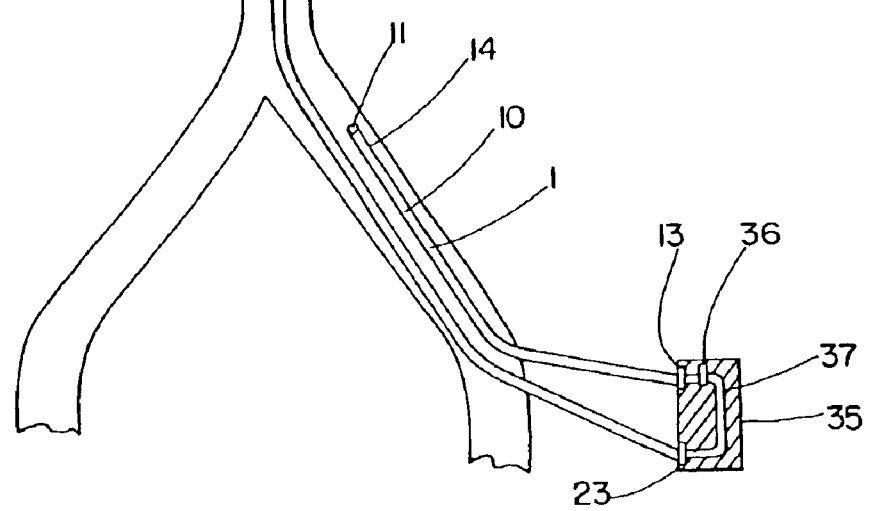

FIG. 4 depicts another embodiment of the device inserted through two separate incisions on the left femoral artery. Tubular members 1 and 2 may be inserted through the same incision or different incisions on the artery. Construction of this device and methods of using it are similar to those described in FIG. 3A except insofar as the tubular members are not carried within a lumen of a catheter. This embodiment may be desirable in situations in which the first tubular member is inserted into a vein, such as the femoral, iliac, axillary or subclavian vein. Deoxygenated blood is aspirated through port 11 and lumen 14 and delivered to an oxygenator. Oxygenated blood is then delivered to pump 35 and to the right carotid artery through lumen 20 and port 22 to provide contralateral perfusion augmentation to the ischemic cerebral tissue distal to occlusion 70. Mild to moderate hypothermia, at approximately 32 to 34° C., can be introduced during the blood recirculation. Neuroprotective agents, administered to the contralateral carotid artery through lumen 20 and port 22, may reach the ischemic region more effectively.

Figure 5A:
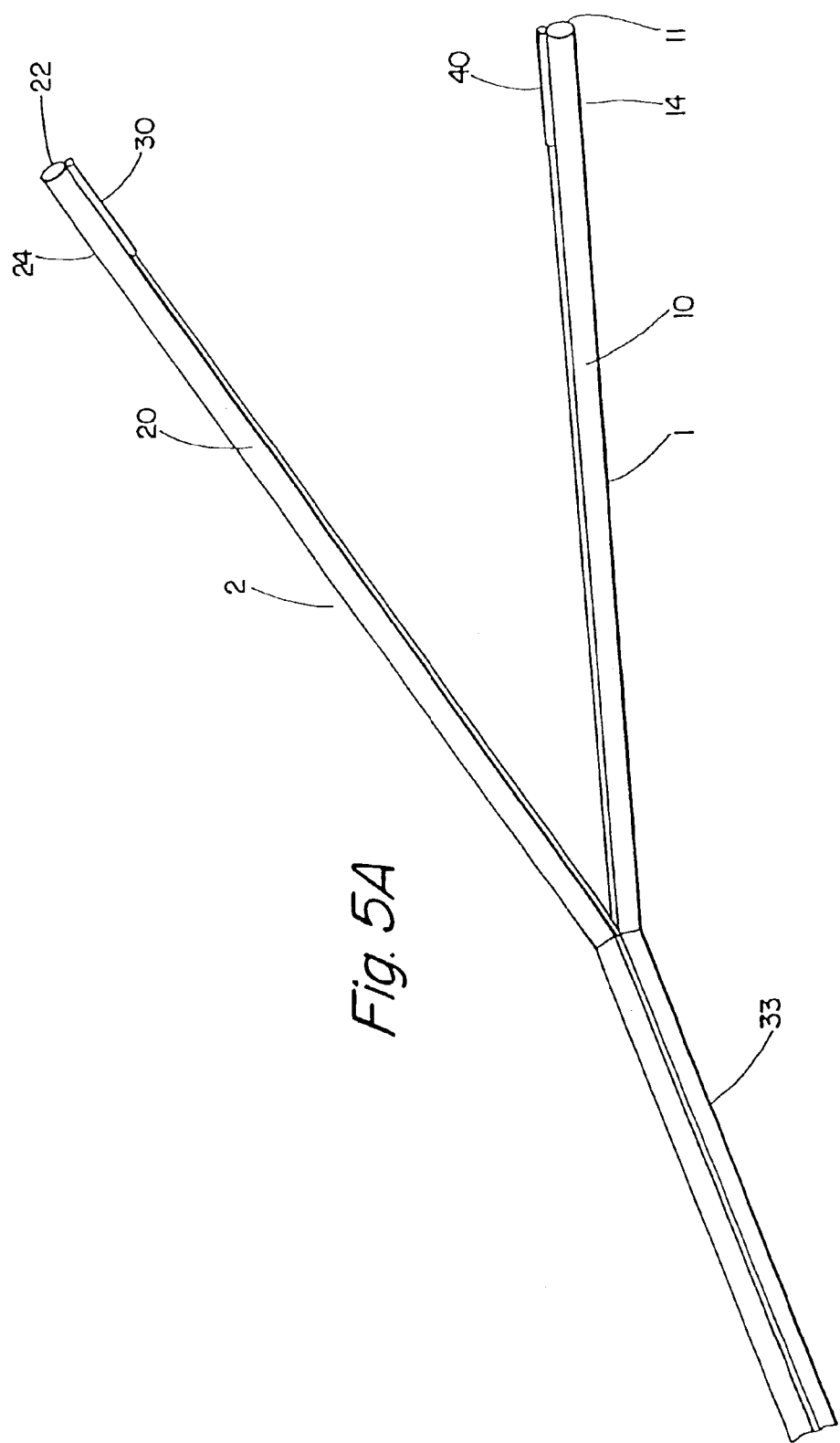
FIG. 5A depicts a distal region of another embodiment of the device for treatment of acute stroke.
Figure 5B:
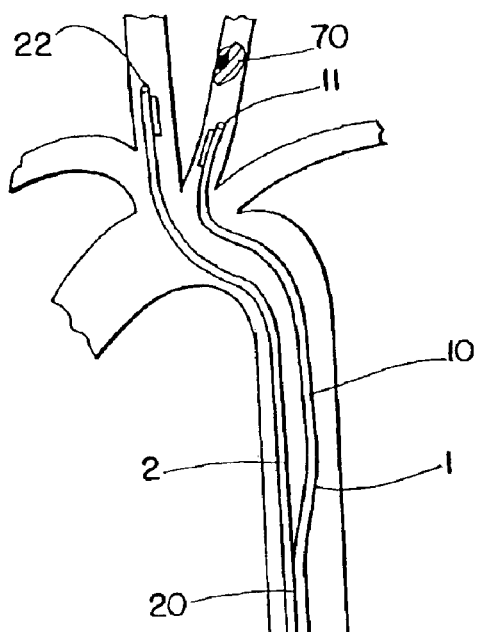
FIG. 5B depicts the device of FIG. 5A inserted into bilateral carotid arteries.
Figure 5B:
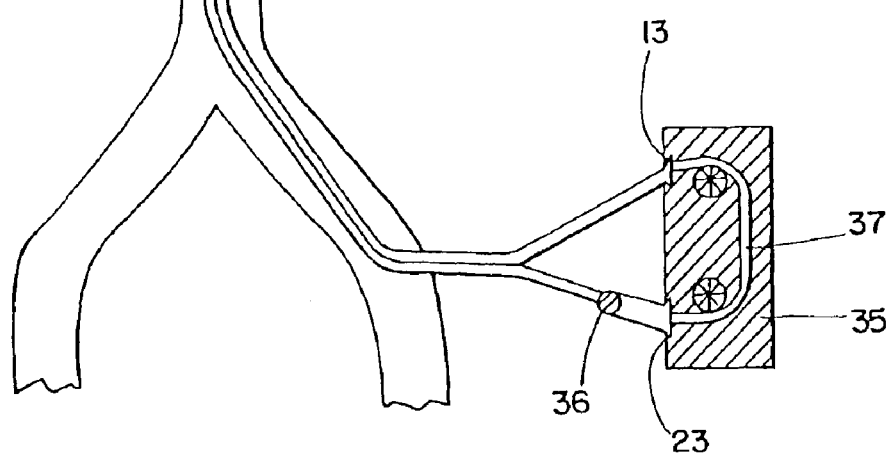

FIGS. 5A and 5B depict still another embodiment of the device, which comprises tubular members 1 and 2. The first tubular member has lumen 10 communicating with distal port 11 and proximal end 13 adapted for aspiration of blood from a carotid or a cerebral artery. The second tubular member has lumen 20 communicating with distal port 22 and proximal end 23 adapted for perfusion of blood to a carotid artery. The first and second tubular members are carried within a lumen of elongate catheter 33. Manometer 30 and manometer 40 are carried respectively at distal end 24 of the second tubular member and distal 14 of the first tubular member for measuring blood pressure at the distal end. Blood filter 36 is included in the proximal end of the second tubular member to capture embolic debris.

In use, the device is inserted through an incision on the left femoral artery as shown in FIG. 5B. The distal end of tubular member 1 is advanced over a guide wire into the left carotid artery until occluding lesion 70 is localized with dye, and the distal end is positioned proximal to the occlusion. The distal end of tubular member 1 can be advanced as far as the occluding site which could be in the common carotid artery, internal carotid artery, middle cerebral artery, anterior cerebral artery, carotid siphon, terminal internal carotid artery, or any other part of the cerebral vasculature. In an emergency, the device can also be inserted into a patient's carotid artery as a direct stick after localizing the occlusion with the assistance of IVUS or standard carotid doppler and transcranial doppler (TCD). The distal end of tubular member 2 is inserted into the right carotid artery, either the CCA or ICA. Proximal end 13 and 23 of the first and second tubular member respectively are attached to pump 35. Blood is aspirated from the occluded carotid artery through lumen 10 and port 11, and delivered to the contralateral carotid artery through lumen 20 and port 22 after it passes through blood filter 36 included in the proximal end of the second tubular member.

The perfusion rate is generally approximately between 7 and 800 cc/min and up to 1.2 liters/min. Heparinization is generally required to prevent thrombi forming in the flow circuit. Any embolic debris is filtered with 100 to 200 micron filter 36 prior to reentry. The augmented contralateral hemispheric blood flow, which reverses flow across the Circle of Willis via ACA, posterior communicating, ophthalmic, and external carotid arteries, provides not only retrograde arterial collateral enhancement to the ischemic area distal to the occlusion, but also enhanced pressure differential across the occlusion, which may be sufficient to dislodge and thereby remove the occluding lesion or any embolic debris in the symptomatic artery. The desired flow rate necessary to reverse flow across the Circle of Willis is modified according to the patient's physical examination, since the patient may develop "steal" symptoms. As blood is aspirated from the symptomatic carotid artery, blood flow may be reduced significantly to result in "steal syndrome," similar to "subclavian steal syndrome" in which significant subclavian stenosis leads to blood flow reversal in the vertebral artery and is redirected away from the brain to the distal subclavian artery with physical activity of the ipsilateral arm. Aspiration of blood is reduced or discontinued if ischemic symptoms ensue.

Figure 6:
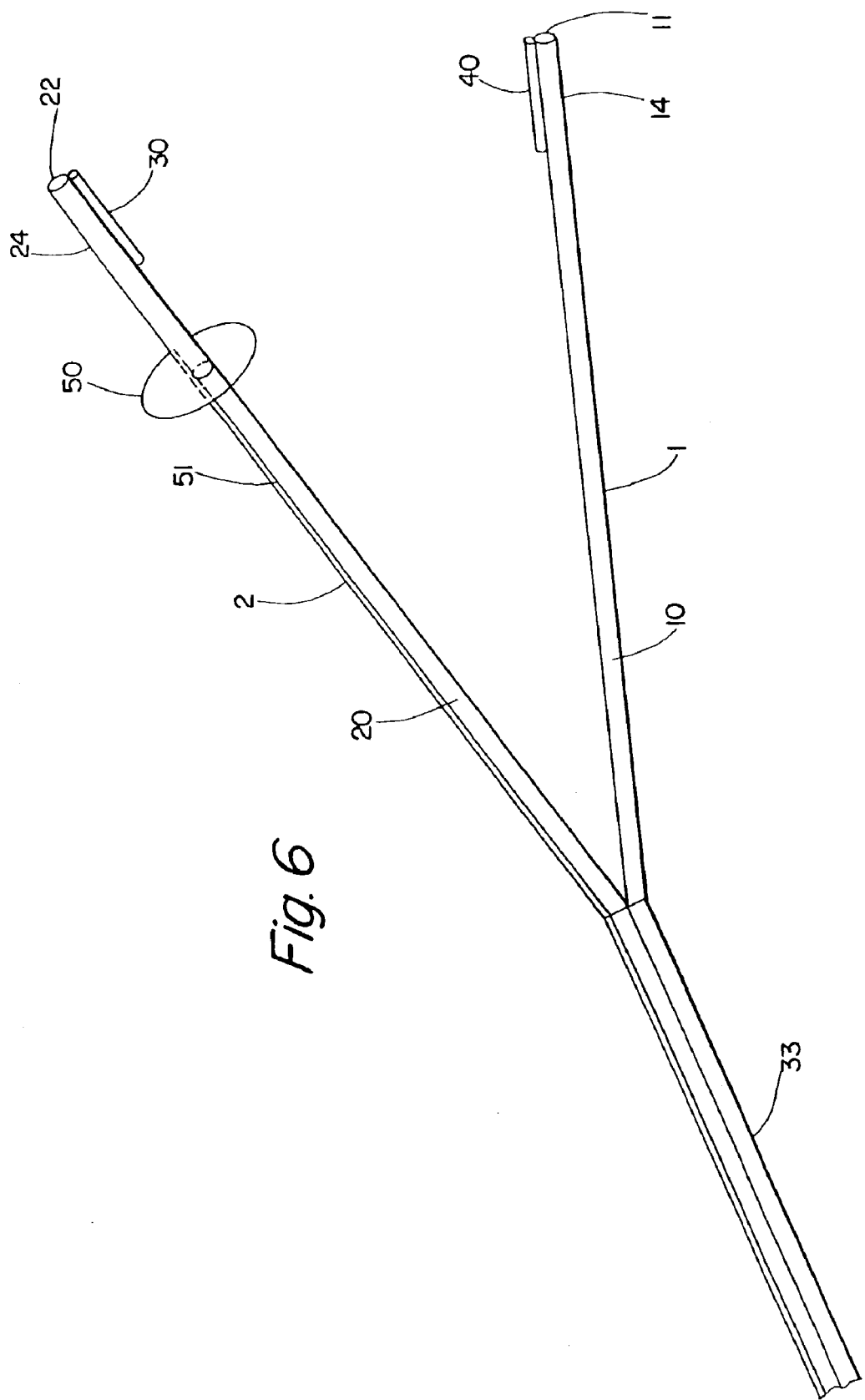
FIG. 6 depicts a distal region of another embodiment of the device having a balloon occluder.

The embodiment depicted in FIG. 6 differs from the embodiment depicted in FIG. 5B in that balloon occluder 50, communicating with inflation lumen 51, is mounted on distal region 24 of the second tubular member proximal to port 22. In use, as the first tubular member is inserted in the symptomatic carotid artery and the second tubular member is inserted in the contralateral carotid artery, the balloon can be inflated to occlude the arterial lumen to reduce run-off of perfused blood and to provide compartmentalization for administration of pharmaceutical agents, such as a neuroprotective agent.

Figure 7A:
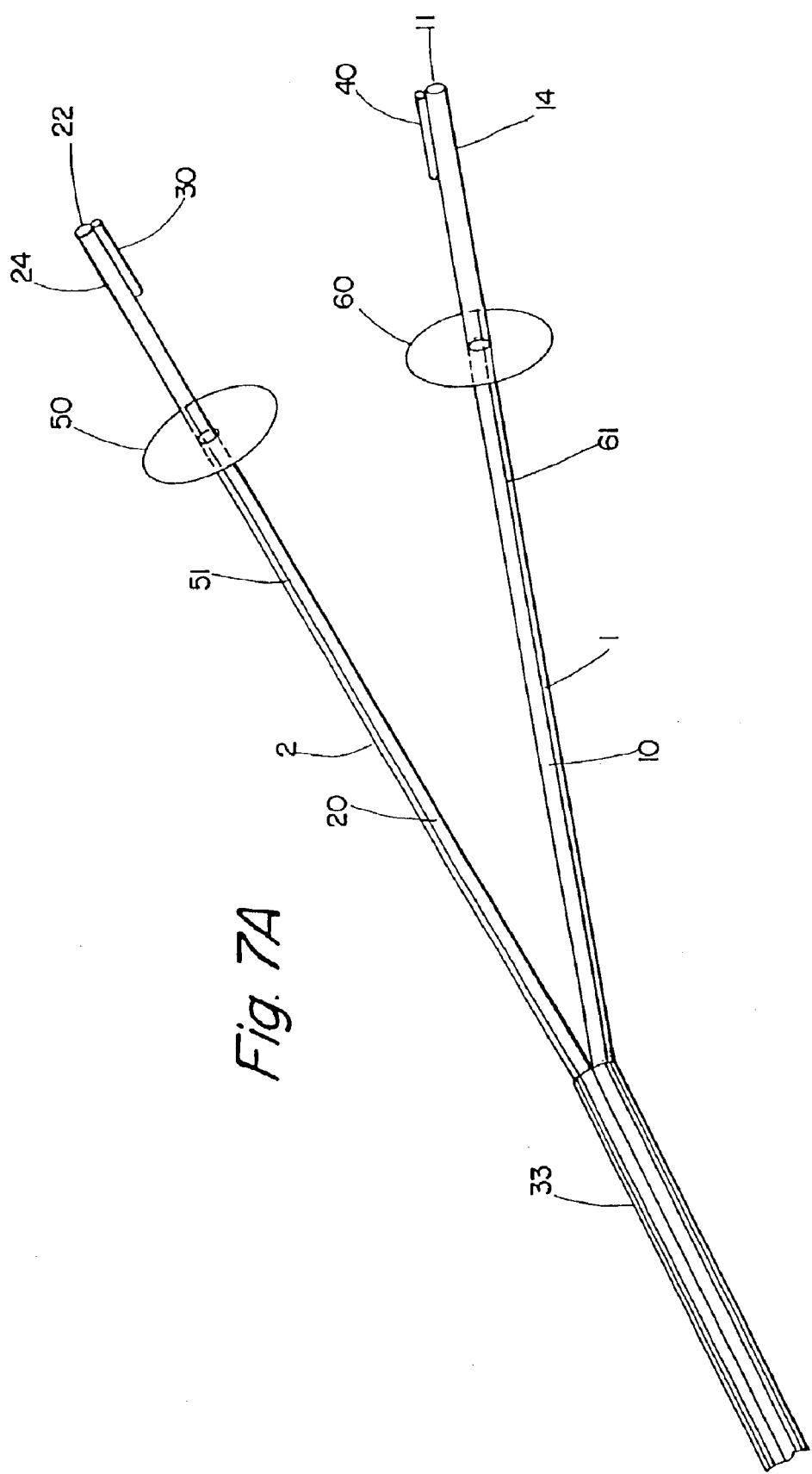
FIG. 7A depicts another embodiment of the device having two balloon occluders.

FIGS. 7A and 7B depict, respectively, a distal and a proximal region of another embodiment of the device for treatment of acute stroke. The device comprises first tubular member 1 and second tubular member 2. The first and second tubular members are carried within a lumen of elongate catheter 33. The first tubular member has lumen 10 communicating with distal port 11 and proximal end 13. The second tubular member has lumen 20 communicating with distal port 22 and proximal end 23. The proximal ends of both tubular members are connected to pump 35 for aspirating blood from the first tubular member and delivering it to the second tubular member through conduit 37. Lumens 10 and 20 further communicate, respectively, with proximal ports 68 and 58, which can be used to administer heparin or neuroprotective agents. Blood filter 36 is included in the proximal end of the first tubular member for capturing embolic material in the blood before returning to the second tubular member. Manometer 30 communicating with sensor attachment 31 is carried at distal end 24 of the second tubular member for measuring blood pressure at the distal end. Likewise, manometer 40 communicating with sensor attachment 32 is carried at distal end 14 of the first tubular member. Balloon occluder 50 communicating with inflation lumen 51 is mounted on the distal end of the second tubular member proximal to port 22. Likewise, balloon occluder 60 communicating with inflation lumen 61 is mounted on the distal end of the first tubular member proximal to port 11.

Figure 7C:
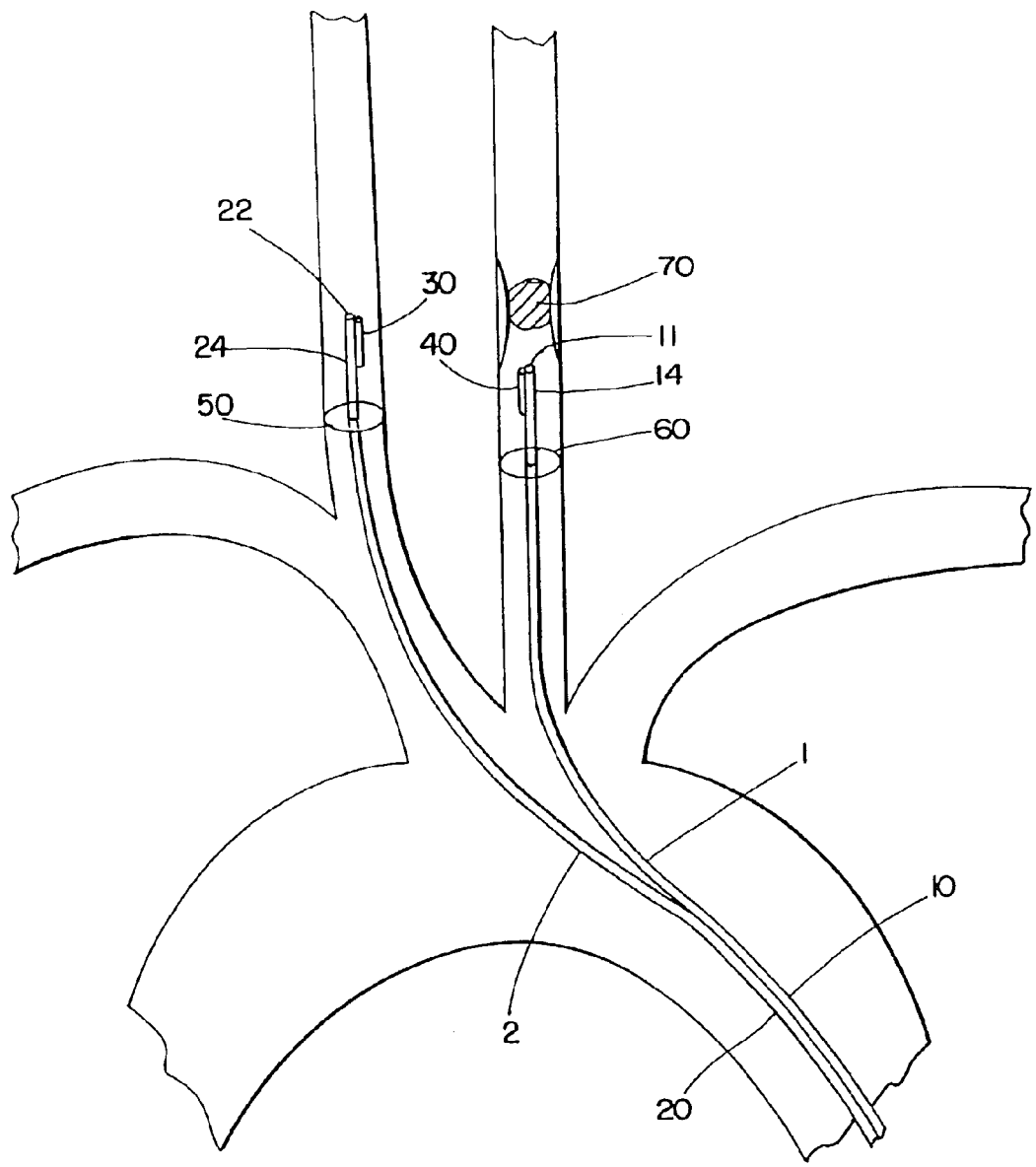
FIG. 7C depicts a distal region of the device in FIG. 7A inserted in the carotid arteries.

In use, distal end 14 of first tubular member 1 is inserted proximal to occluding lesion 70 in the left carotid artery and distal end 24 of second tubular member 2 is inserted in the right carotid artery as shown in FIG. 7C. Blood is aspirated from the occluded artery through port 11 and lumen 10 of the first distal member, passed through the blood filter included in the proximal end of the first tubular member, and returned to the contralateral artery through lumen 20 and port 22 via the pump. Balloon 50 on the second tubular member can be inflated to (1) prevent run-off of the perfused blood, (2) control flow rate to the contralateral artery, e.g., the flow rate decreases as the balloon is deflated, and (3) provide complete compartmentalization for more efficacious administration of pharmacotherapy to the cerebral tissues. An atherectomy device may be introduced through an additional lumen (not shown) included in the first tubular member to remove the occluding lesion. Balloon 60 on the first tubular member can be inflated or deflated to (1) control the flow rate of aspirated blood, e.g., the flow rate increases as the balloon is deflated, (2) increase negative pressure proximal to the occlusion, thereby enhancing the pressure gradient across the occlusion, which may dislodge the offending lesion, and (3) assist in removing tissue or atheromatous debris generated during atherectomy, thereby reducing embolization to the distal arteries.

Figure 8A:
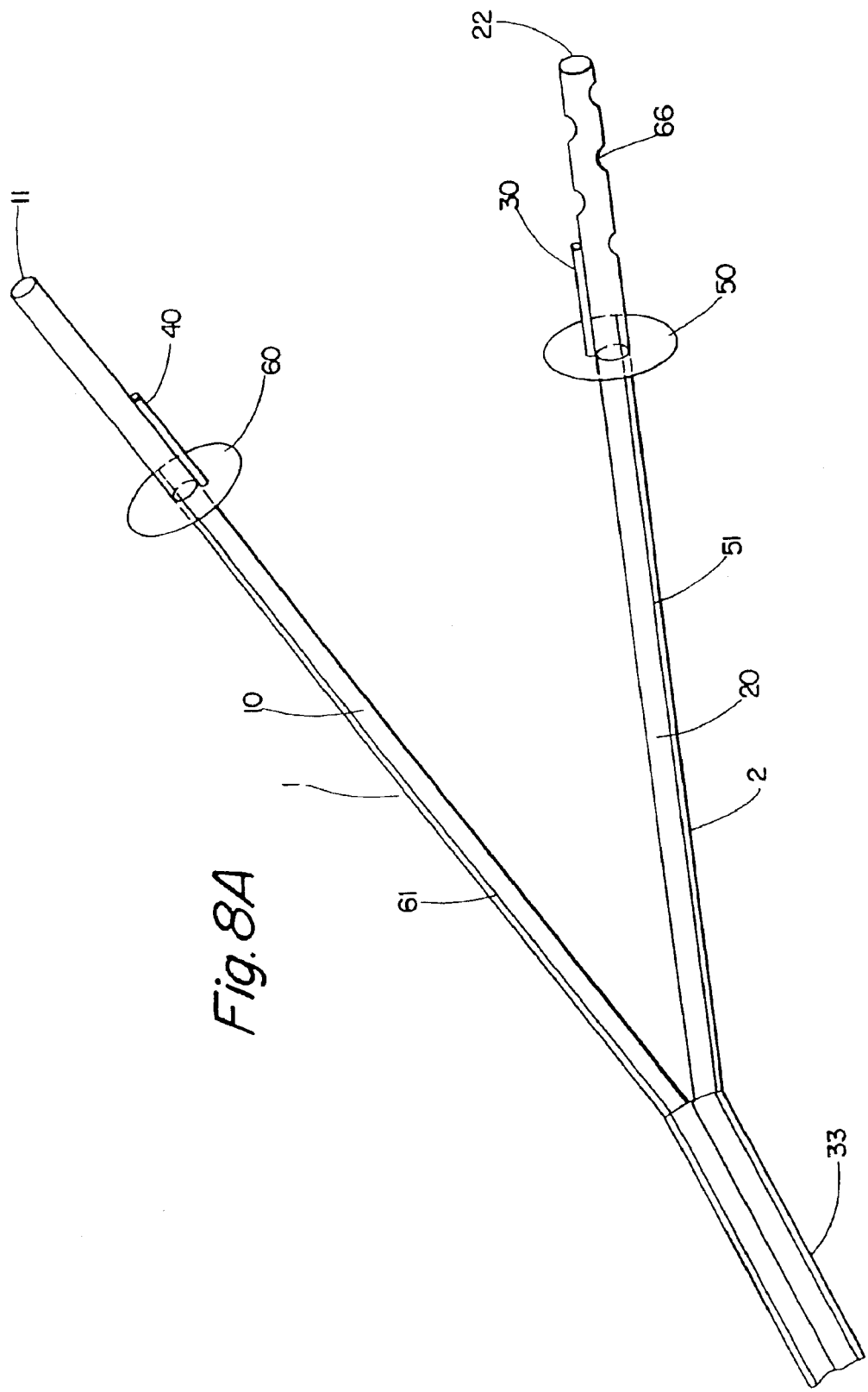
FIG. 8A depicts still another embodiment of the device having two balloon occluders and a plurality of perfusion ports on one of the tubular members.

FIGS. 8A and 8B depict still other embodiments of the device having a plurality of ports. The embodiments comprise balloon occluders 50 and 60, communicating respectively with inflation lumen 51 and 61, mounted on first tubular member 1 and second tubular member 2. In FIG. 8A, lumen 10 of the first tubular member communicates with port 11 distally. Lumen 20 of the second tubular member communicates with 1, 2, 3, 4, 5, 6, or other number of perfusion ports 66 distally to provide more efficient delivery of perfused blood to the contralateral carotid artery. In FIG. 8B, lumens 10 and 20 of the first and second tubular members communicate, respectively, with distal port 11 and 22, and with 1, 2, 3, 4, 5, 6, or other number of perfusion ports 66 distally; in which case the ports can be used to aspirate blood from the symptomatic carotid artery or perfuse blood to the contralateral carotid artery.

In patients with vertebral artery occlusions, treatment with angioplasty often results in disastrous complications due to embolization of the occlusive lesion downstream to the basilar artery. Emboli small enough to pass through the vertebral arteries into the larger basilar artery are usually arrested at the top of the basilar artery where it bifurcates into the posterior cerebral arteries. The resulting reduction in blood flow to the ascending reticular formation of the midbrain and thalamus produces immediate loss or impairment of consciousness. The devices and methods described above can be used to (1) maintain perfusion to an ischemic region by enhancing blood flow to the contralateral artery when ipsilateral perfusion can not be augmented, (2) remove thromboembolic material from the vertebral artery, or (2) provide protection during angioplasty and/or stenting by occluding the artery, reversing the flow and so preventing emboli from progressing through the basilar artery.

Figure 9:
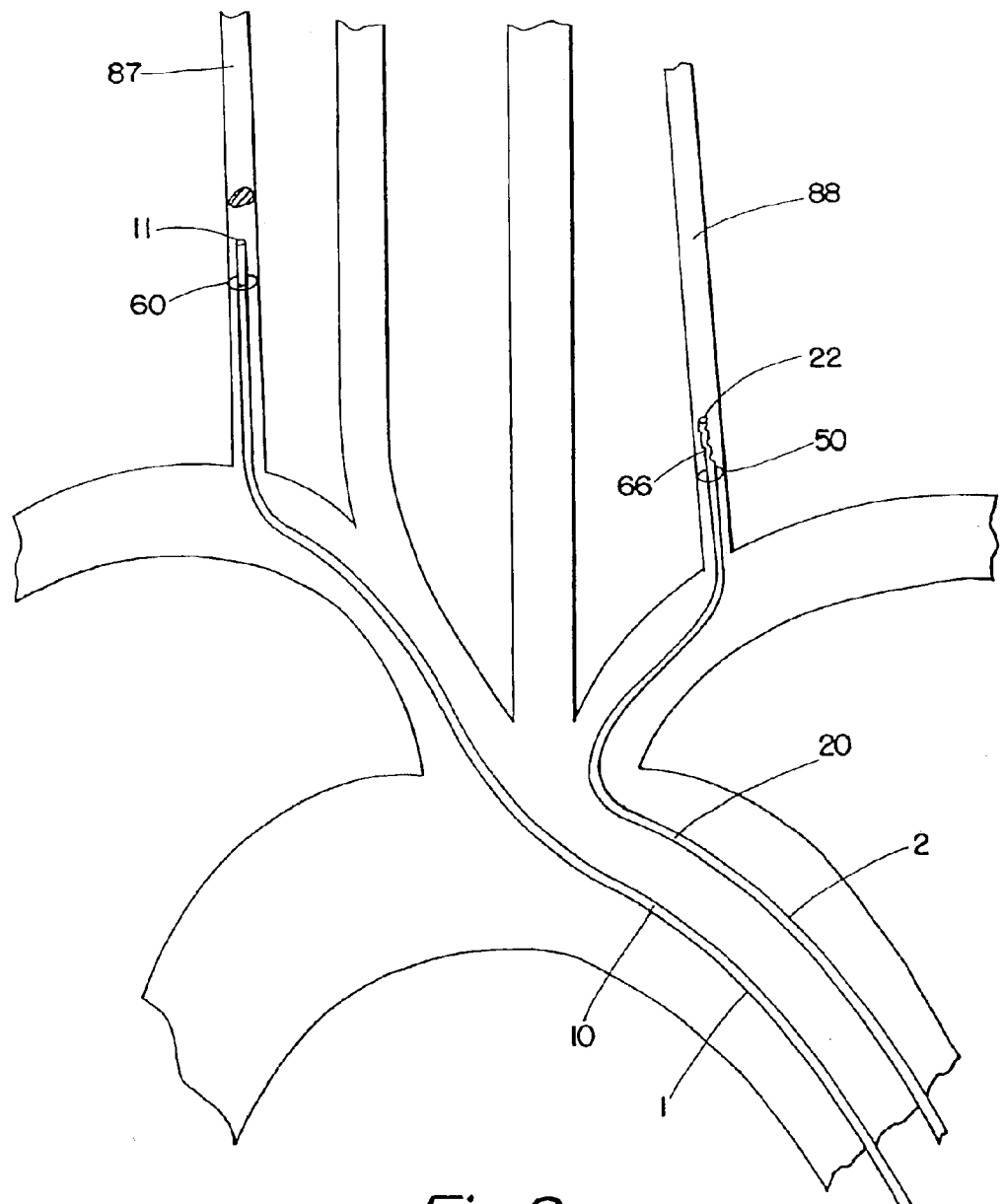
FIG. 9 depicts the device of FIG. 8B inserted in the vertebral arteries.

In using the device of FIG. 8A, for example, the occluding lesion is first localized with transcranial doppler or angiogram. Distal end 14 of first tubular member 1 is shown inserted proximal to thromboembolic material 70 in right vertebral artery 87 as shown in FIG. 9. Distal end 24 of second tubular member 2 is inserted in left vertebral artery 88. Alternatively, distal end 14 can be inserted in the right brachiocephalic or the right subclavian artery, and distal end 24 can be inserted in the left subclavian or the left carotid artery. Proximal ends of both tubular members are attached to a pump for aspirating blood from the occluded vertebral artery and returning to the contralateral vertebral artery. Balloon occluders 50 and 60 can be inflated to control the flow rate. In this manner, perfusion to the ischemic area distal to the occlusion is maintained by enhancing blood flow to the contralateral artery, thereby opening collateral arteries and reversing flow across the Circle of Willis to the symptomatic vertebral artery. Alternatively, distal end 24 can be inserted in the ipsilateral carotid artery when perfusion to the ischemic region via ipsilateral collaterals can be augmented. By applying suction to the distal end of the first tubular member, the pressure gradient across the occluding lesion increases and thromboembolic material 70 may be dislodged onto the distal port and be removed. By using the devices and methods with an angioplasty or atherectomy device to remove a thromboembolic lesion in the vertebral artery, embolization from the vertebral distally to the basilar artery may be minimized.

Figure 10:
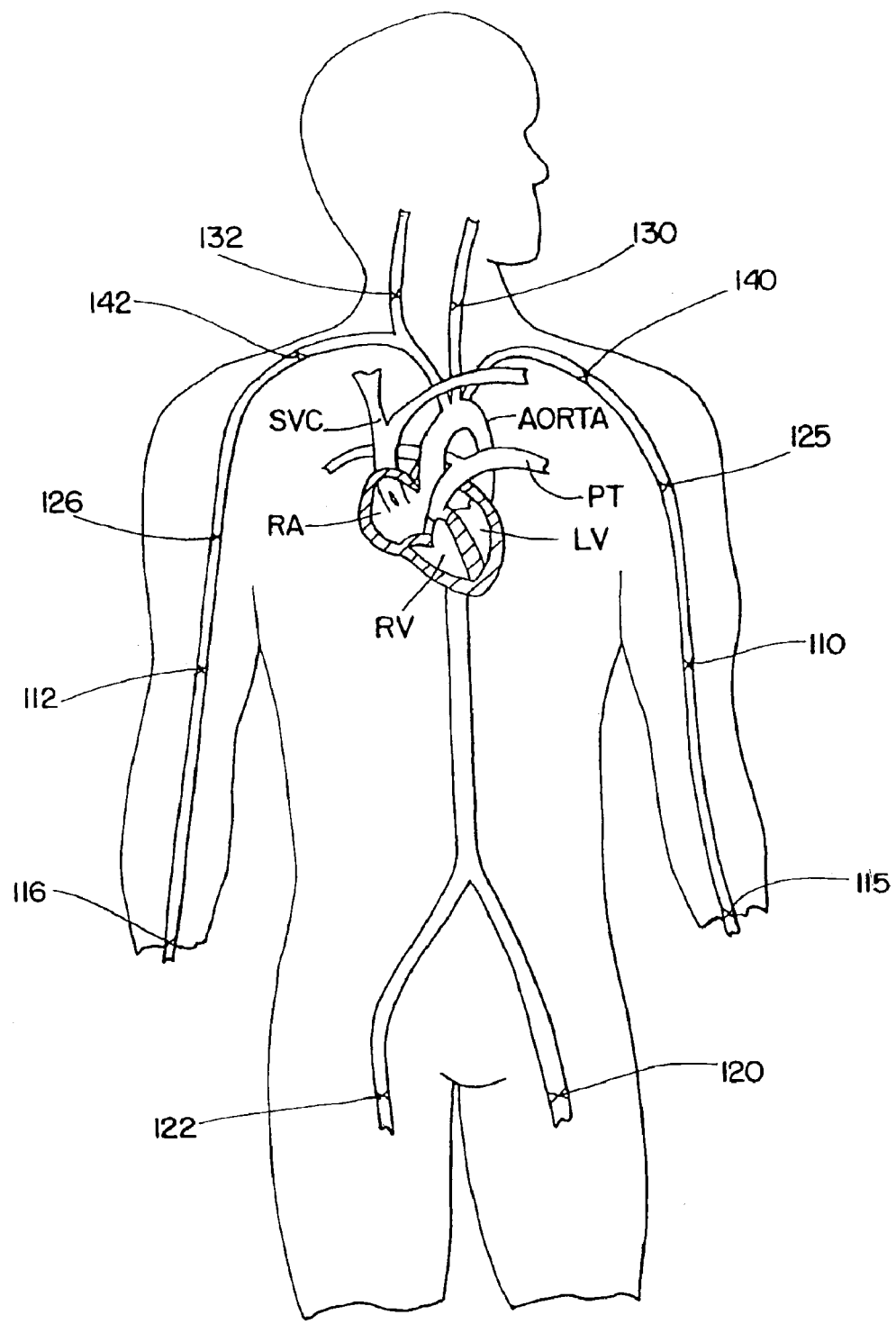
FIG. 10 depicts different peripheral artery access sites for insertion of the device.

FIG. 10 depicts different sites of entry for the devices disclosed herein. An incision can be made on a peripheral artery, such as right femoral artery 122, left femoral artery 120, right radial artery 116, left radial artery 115, right brachial artery 112, left brachial artery 110, right axillary artery 126, left axillary artery 115, right subclavian artery 142, or left subclavian artery. An incision can also be made on right carotid artery 132 or left carotid artery 130 in emergency situations.

The length of either tubular member will generally be between 10 and 200 centimeters, preferably approximately between 30 and 150 centimeters. The inner diameter of the tubular member will generally be between 0.2 and 0.7 centimeters depending on the desired perfusion rate, preferably approximately between 0.3 and 0.5 centimeters. The diameter of the expanded occluder will generally be between 0.3 and 2 centimeters, preferably approximately 0.5 and 1.0 centimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method for augmenting circulation in a patient having a vascular lesion, comprising the steps of:

providing an elongate tubular member having a lumen communicating with a port at a distal end;

inserting the tubular member into a peripheral artery and advancing the distal port into a first cerebral or carotid artery substantially free of a lesion, wherein the patient possesses a second cerebral or carotid artery substantially occluded by a lesion; and perfusing blood into the first cerebral or carotid artery through the tubular member, wherein contralateral flow is augmented to improve perfusion to an ischemic region distal to the lesion by retrograde blood flow within the second cerebral or carotid artery.

2. The method of claim 1, wherein a proximal end of the tubular member is attached to a pump.

3. The method of claim 1, wherein blood is aspirated from an artery and filtered before perfusion into the carotid artery.

4. The method of claim 1, wherein the lesion is located in the internal carotid artery.

5. The method of claim 1, wherein the lesion is located in the middle cerebral artery.

6. The method of claim 1, wherein the tubular member further includes a manometer carried at the distal end.

7. The method of claim 1, wherein the tubular member further includes an expandable occlusive member carried proximal to the distal port.

8. The method of claim 7, wherein the step of inserting the tubular member into an artery further comprises the step of expanding the occlusive member.

9. The method of claim 7, wherein the step of advancing the port of the tubular member into the carotid artery further comprises the step of expanding the occlusive member.

10. The method of claim 1, wherein the blood perfused into the carotid artery is hypothermic.

11. The method of claim 1, wherein the port and lumen of the tubular member are adapted for infusion of fluid and pharmaceutical agents.

12. The method of claim 11, wherein the pharmaceutical agent is a neuroprotective agent.

13. The method of claim 11, wherein the pharmaceutical agent is heparin.

14. The method of claim 1, further comprising the steps of inserting a second tubular member into an artery and aspirating blood from the artery through the second tubular member.

15. The method of claim 1, wherein the lesion is a stenosis, thrombus, and/or emboli.

16. The method of claim 1, further comprising the step of performing an angioplasty procedure in the second carotid artery to open the lesion.

17. The method of claim 1, further comprising the step of placing a stent in the second carotid artery to open the lesion.

18. A method for augmenting circulation in a patient having carotid stenosis, comprising the steps of:

provliding a first elongate tubular member having a lumen communicating with a port at a distal end;

providing a second elongate tubular member having a lumen communicating with a port at a distal end;

inserting the first tubular member into a peripheral artery;

inserting the second tubular member into the peripheral artery and advancing the distal port into a first carotid artery substantially free of a lesion, wherein the patient possesses a second carotid artery substantially occluded by a lesion; and perfusing blood into the first carotid artery through the second tubular member, wherein contralateral flow is augmented to improve perfusion to an isehemic region distal to the lesion by retrograde blood flow within the second carotid artery.

* * * * *